(12) United States Patent
Khavinson et al.

(10) Patent No.: US 8,057,810 B2
(45) Date of Patent: Nov. 15, 2011

(54) PEPTIDE SUBSTANCE REVEALING AN IMMUNOGEROPROTECTIVE EFFECT, PHARMACEUTICAL COMPOSITION ON ITS BASE AND THE METHOD OF ITS APPLICATION

(75) Inventors: Vladimir Khatskelevich Khavinson, St. Petersburg (RU); Evgeny Iosifovich Grigoriev, St. Petersburg (RU); Vladimir Victorivich Malinin, St. Petersburg (RU); Galina Anatolievna Ryzhak, St. Petersburg (RU)

(73) Assignee: Obschestvo S Ogranichennoi Otvetstvennostyu "Sia Peptides", Saint-Petersburg (RU)

( * ) Notice: Subject to any disclaimer, the term of this patent is extended or adjusted under 35 U.S.C. 154(b) by 506 days.

(21) Appl. No.: 12/298,423

(22) PCT Filed: Mar. 2, 2007

(86) PCT No.: PCT/RU2007/000099
§ 371 (c)(1),
(2), (4) Date: Oct. 24, 2008

(87) PCT Pub. No.: WO2007/139435
PCT Pub. Date: Dec. 6, 2007

(65) Prior Publication Data
US 2009/0170785 A1 Jul. 2, 2009

(30) Foreign Application Priority Data
May 30, 2006 (RU) .................................. 2006118488

(51) Int. Cl.
*A61K 38/06* (2006.01)
*C07K 5/093* (2006.01)
(52) U.S. Cl. ..................... 424/278.1; 514/21.9; 530/331
(58) Field of Classification Search ........................ None
See application file for complete search history.

(56) References Cited

U.S. PATENT DOCUMENTS
6,727,227 B1 4/2004 Khavinson

FOREIGN PATENT DOCUMENTS
| WO | WO 01/47950 A | 6/2001 |
| WO | WO 2005/056580 A | 6/2005 |
| WO | WO 2006/001728 A | 1/2006 |
| WO | WO 2007/136294 A1 | 11/2007 |
| WO | WO 2007/136295 A2 | 11/2007 |
| WO | WO 2007/139431 A1 | 12/2007 |

OTHER PUBLICATIONS

Ruiz-Alcaraz et al. Gonadins, a novel family of glutamyl-tripeptide amides . . . Regulatory Peptides. 2005, vol. 129, pp. 93-101.*
Mileusnic, R. et al., "The Peptide Sequence Arg-Glu-Arg, Present in the Amyloid Precursor Protein, Protects Against Memory Loss Caused by Abeta and Acts as a Cognitive Enhancer" European Journal of Neuroscience, Apr. 2004, pp. 1933-1938, vol. 19, No. 7, Oxford University Press, Great Britain.
Khavinson, V Kh. et al., "Mechanisms Underlaying Geroprotective Effects of Peptides" Bulletin of Experimental Biology and Medicine, Jan. 2002, pp. 1-5, vol. 133, No. 1, Consultants Bureau, New York, NY.
Korkushko O. V. et al., "Geroprotective Effect of Epithalamine (Pineal Gland Peptide Preparation) in Elderly Subjects with Accelerated Aging" Bulletin of Experimental Biology and Medicine, Sep. 1, 2006, pp. 356-359, vol. 142, No. 3, Kluwer Academic Publishers, NE.
Wang Chao et al., "The Synthesis and Immunosuppressive Activities of Steroid-urotoxin Linkers" Bioorganic & Medicinal Chemistry, Aug. 15, 2004, pp. 4403-4421, vol. 12, No. 16.
Barabanova, S.V. et al., "[Parallel Analysis of C-Fos Protein and Interleukin-2 Expression in Hypothalmic Cells Under Different Influence]" Feb. 2007, pp. 150-160, vol. 92, No. 2, Rossi §SKII Fiziologicheski § Zhurnal Imeni I.M. Sechenova, Rossi §Skaia Akademiia Nauk.
Sibarov, D.A. et al., "Epitalon Influences Pineal Secretion in Stress-Exposed Rats in the Daytime" Neuroendocrinology Letters, 2002, pp. 452-454, vol. 23, No. 5-6, Sweden.
Abiko, Takashi, et al., "Characterization of an Acidic Tripeptide in Neutotoxic Dialysate," *Chemical & Pharmaceutical Bulletin*, vol. 28, No. 5, May 1980, pp. 1629-1633.

* cited by examiner

*Primary Examiner* — Jeffrey E Russel
(74) *Attorney, Agent, or Firm* — Leydig, Voit & Mayer, Ltd.

(57) ABSTRACT

Disclosed is a pharmaceutical composition for the prevention and correction of age-related disorders of cellular and humoral immunity and having an immunogeroprotective effect. The pharmaceutical composition includes a peptide glutamyl-aspartyl-proline with general formula H-Glu-Asp-Pro-OH sequence 1 [SEQ ID NO:1]. The pharmaceutical composition can be in the form suitable for parenteral administration. Also disclosed is a method of prevention and/or correction of age-related disorders of cellular and humoral immunity by stimulating the processes of lymphocytes proliferation and differentiation, such method consisting in the administration to a patient of a pharmaceutical composition containing an effective amount of peptide glutamyl-aspartyl-proline with general formula: H-Glu-Asp-Pro-OH sequence 1 [SEQ ID NO:1] in the dose of 0.01-100 µg/kg of body weight as an active base at least once a day during a period necessary for attaining a therapeutic effect.

5 Claims, 1 Drawing Sheet

Fig. 1

* - P<0.05 as compared to the control taken as 100%.

Fig. 2

* - P<0.05 as compared to the control taken as 100%.

PEPTIDE SUBSTANCE REVEALING AN IMMUNOGEROPROTECTIVE EFFECT, PHARMACEUTICAL COMPOSITION ON ITS BASE AND THE METHOD OF ITS APPLICATION

The invention is related to the medicinal means of prevention and correction of age-related disorders of cellular and humoral immunity and may be used as a medication revealing an immunogeroprotective effect.

Disordered functioning of both immune system as a whole and of its certain segments is considered to be one of the main causes of ageing. Ageing is accompanied by an involution of immune system organs, first of all of the thymus [Petrov R. V., Khaitov R. M. Immune response and ageing//Advances of modern biology.—1975.—V. 79, issue 1.—pp. 111-127 (rus.); Hirokawa K. Thymus and ageing//Immunology and ageing./Ed. by. T. Macinodan and E. Yunis.—Moscow, Mir Publishing House, 1980.—pp. 75-101 (rus.)]. Age-related involution of the thymus is characterized by reduced functional activity of T-lymphocytes, disordered protein synthesis in the lymphocytes, altered proportion of immunocompetent cells subpopulations and a decline of immunoregulatory peptides production. Age-related alterations of immune reactivity are related to the disordered structure and function of the genes, which control the immune response, including histocompatibility system genes. [Dontsov V. I., Krut'ko V. N., Podkolzin A. A. Fundamental mechanisms of geroprophylactics.—Moscow, Bioinformservis Publishing House, 2002. p. 464 (rus.)].

Therapeutic potential of many peptide medications is known to be manifested in the stimulation of immunity and reparative processes. Peptides evoke metabolic changes, which are controlled via the mechanisms of gene regulation [Khavinson V. Kh. Malinin V. V. Gerontological Aspects of Genome Peptide Regulation.—Base 1: Karger, 2005.—104 p.].

There are known immunostimulators of peptide nature: Tactivin (FR Patent No. 2570278), Thymosin (Goldstein A. L. et.al, Proc. Nat. Acad. Sci. USA, 1972, v. 69, p. 1856-1863). These preparations are a set of polypeptides with different lengths effective on different segments of the immune response, as well as on other physiological functions of the organism, which leads to unfavorable side effects. It is also noteworthy, that these medications are obtained from natural materials, which makes their practical usage more complicated due to the complexity of their isolation, low output and significant variability of their physico-chemical properties.

There are known synthetic peptide imnunostimulators—analogues of Thymopeptin (U.S. Pat. No. 5,013,723), Thymogen (RU Patent No. 1737798, EP No. 0445581).

Immune system disorders are associated with many diseases occurring in older and very old age, first of all autoimmune diseases, tumors, diseases of joints, kidneys, as well as amyloidosis, cardiovascular pathology, infective diseases. Broadening range of adverse impacts on human organism entails premature ageing and accelerated development of age-related pathology.

In this connection, the design of effective immunogeroprotectors is presently of ever growing importance.

The proposed peptide has no structural analogues in the prior art.

This invention has set and resolved the objective of obtaining a new peptide, revealing an immunogeroprotective effect.

Technical result of the invention consists in the creation of a new peptide, revealing an immunogeroprotective effect, as well as of a pharmaceutical composition, containing this peptide as its active base, such composition being capable of stimulating the processes of lymphocytes proliferation and differentiation by restoring the synthesis of tissue specific proteins, by normalizing metabolic and molecular-genetic indices in case of age-related disorders of cellular and humoral immunity.

This invention is related to a peptide glutamyl-aspartyl-proline with general formula: H-Glu-Asp-Pro-OH sequence 1 [SEQ ID NO:1].

Peptide glutamyl-aspartyl-proline with general formula: H-Glu-Asp-Pro-OH sequence 1 [SEQ ID NO:1] reveals an immunogeroprotective effect.

Peptide glutamyl-aspartyl-proline with general formula: H-Glu-Asp-Pro-OH sequence 1 [SEQ ID NO:1] is proposed for manufacturing a pharmaceutical composition, reveals an immunogeroprotective effect.

The other aspect of this invention is related to a pharmaceutical composition revealing an immunogeroprotective effect, characterized in that such composition contains an effective amount of peptide glutamyl-aspartyl-proline with general formula: H-Glu-Asp-Pro-OH sequence 1 [SEQ ID NO:1] as its active base, as well as a pharmaceutically acceptable carrier.

In this case such pharmaceutical composition exists in the form suitable for parenteral administration.

The next aspect of this invention is related to a method of prevention and/or correction of age-related disorders of cellular and humoral immunity by stimulating the processes of lymphocytes proliferation and differentiation, such method consisting in the administration to a patient of a pharmaceutical composition containing an effective amount of peptide glutamyl-aspartyl-proline with general formula: H-Glu-Asp-Pro-OH sequence 1 [SEQ ID NO:1] in the dose of 0.01-100 µg/kg of body weight as an active base at least once a day during a period necessary for attaining a therapeutic effect.

In this case the pharmaceutical composition is administered parenterally.

Peptide glutamyl-aspartyl-proline with general formula: H-Glu-Asp-Pro-OH is obtained using a classical method of peptide synthesis in a solution.

The possibility of objective attainment of the technical result by using the invention is substantiated by reliable data indicated in examples, which contain experimental data obtained in the studies performed using the methods, which are universally accepted in this field of knowledge.

Peptide glutamyl-aspartyl-proline with amino acid sequence: H-Glu-Asp-Pro-OH reveals a biological activity, namely it exerts an immunogeroprotective effect by stimulating the processes of lymphocytes' proliferation and differentiation by restoring the synthesis of tissue specific proteins, by normalizing the metabolic and molecular-genetic indices in case of age-related disorders of cellular and humoral immunity.

Stimulating effect of peptide H-Glu-Asp-Pro-OH on the functional activity of lymphocytes was revealed by its experimental study.

Biological activity of peptide H-Glu-Asp-Pro-OH was studied on thymus explants, on the culture of epithelial thymus cells, in the experimental model of irradiation induced ageing and on lymphocytes taken from very old patients.

The notion "pharmaceutical composition" implies such different medicinal forms containing the new peptide, which may find therapeutic application as a medication revealing an immunogeroprotective effect.

To obtain pharmaceutical compositions according to this invention, an effective amount of peptide H-Glu-Asp-Pro-OH as the active base (active substance) is mixed with a pharmaceutically acceptable carrier according to methods of compounding, which are traditional for pharmaceutics.

The notion "effective amount" implies the use of such amount of the active base, which must be effective in this medicinal form according to the quantitative indices of its activity and toxicity, as well as basing on the knowledge of a specialist in this field.

The carrier may have different forms, depending on the medicinal form of the medication, which is desirable for administration into the organism.

In case of parenteral administration, the carrier normally includes physiological saline solution or sterile water, although other ingredients promoting stability or preserving sterility may also be included.

The subject matter of the invention is elucidated by figures and tables.

Table 1 illustrates the effect of peptide H-Glu-Asp-Pro-OH on the proliferation of thymus epithelial cells subjected to 1, 4 and 7 passages.

Table 2 illustrates the effect of peptide H-Glu-Asp-Pro-OH on chromatin in the lymphocytes taken from very old patients.

Table 3 shows the effect of peptide H-Glu-Asp-Pro-OH on morphological and biochemical indices of guinea pig peripheral blood in the study of toxicity.

Table 4 displays the effect of peptide H-Glu-Asp-Pro-OH on the indices of cellular and humoral immunity in older and very old patients subjected to small doses of ionizing irradiation.

The invention is illustrated by an example of synthesis of peptide with formula glutamyl-aspartyl-proline (H-Glu-Asp-Pro-OH) (Example 1), examples of study of biological activity of the peptide (Examples 2, 3, 4, 5, 6), example of toxicity (Example 7) and an example of clinical administration of the peptide, demonstrating its pharmacological properties and substantiating the possibility of attaining a therapeutic effect (Example 8).

EXAMPLE 1

Synthesis of Peptide H-Glu-Asp-Pro-OH

1. Compound name: glutamyl-aspartyl-proline.
2. Structural formula: H-Glu-Asp-Pro-OH 3. Molecular formula without ion pair: $C_{14}H_{21}N_3O_8$.
4. Molecular weight without ion pair: 359.33.
5. Ion pair: acetate.
6. Appearance: white amorphous powder without smell.
7. Method of synthesis: the peptide is obtained using a classical method of synthesis in the solution according to the following scheme:

BOC—tert.butyloxycarbonyl group,
OSu—N-oxysuccinimide ester,
DCC—N,N'-dicyclohexylcarbodiimide,
OBzl—benzyl ester,
TFA—trifluoracetic acid,
HOBt—N-oxybenzotriazol.
Characteristics of the ready substance:
    base substance content: 97.19% (by HPLC, 220 nm),
    TCX—individual, $R_f$=0.67 (acetonitrile-water 2:1),
    humidity content: 6%,
    pH of 0.01% solution: 4.7,
    Specific rotary power: $[\alpha]_D^{22}$: −29° (c=1, $H_2O$), "Polamat A", Carl Zeiss Jena.

EXAMPLE OF SYNTHESIS

1) BOC-Glu(OBzl)-OSu, N-oxysuccinimide ester of N-tert.butyloxycarbonyl-(γ-benzyl)glutamic acid (I)

N-tert.butyloxycarbonyl-(γ-benzyl)glutamic acid BOC-Glu(OBzl)-OH (33.7 g, 0.1 mole) is dissolved in 50 ml of N,N'-dimethylformamide, cooled down to the temperature of −10° C.; cooled (4-6° C.) solutions of N,N'-dicyclohexylcarbodiimide (23.0 g, 0.11 mole)in 20 ml of N,N'-dimethylformamide are added while stirring. Reactive mixture is stirred for 12 hours on ice, and then for 24 hours more at room temperature. Fallout N,N'-dicyclohexylurea is filtered out, and the obtained activated ester solution is used without extraction during the next stage.

2) BOC-Glu(OBzl)-Asp(OBzl)-OH, N-tert.butyloxycarbonyl-(γ-benzyl)glutamyl-(β-benzyl)aspartate (II)

(β-benzyl)asparaginic acid H-Asp(OBzl)-OH (28.0 g, 0.12 mole) and 36 ml (0.12 mole) of triethylamine is suspended in 50 ml of N,N'-dimethylformamide and stirred for 1 hour. Then portions of activated ester BOC-Glu(OBzl)-Osu (I) solution, which was obtained during the previous stage, is added. Reactive mixture is stirred at room temperature for 48 hours. Then it is acidified with 0.5 N sulfur acid up to pH 2-3 and extracted with ethyl acetate 4×50 ml. Extracts are combined and successively washed with 0.5 N $H_2SO_4$ 3×50 ml, water 2×50 ml, 5% $NaHCO_3$ solution 2×50 ml, water 2×50 ml, saturated NaCl solution 2×50 ml. Organic layer is dried over $Na_2SO_4$, solvent is removed in vacuum, residue is crystallized over hexane. 50 g of the product (92%) are obtained. $R_f$=0.34 (benzene-acetone 2:1).

3) BOC-Glu(OBzl)-Asp(OBzl)-Pro-OBzl (III), Benzyl Ester of N-tert.butyloxycarbonyl-(γ-benzyl) glutamyl-(β-benzyl)aspartyl-proline (III)

1.2 g (2.2 mmole) of dipeptide and 0.40 g (3 mmole) of oxybenzotriazol are dissolved in tetrahydrofuran (5 ml) and cooled down to the temperature of −10° C. 0.62 g (3 mmole) of dicyclohexylcarbodiimide is dissolved in 5 ml of tetrahydrofuran and cooled down to the same temperature. 0.84 g (3.5 mmole) of proline benzyl ester tosylate is dissolved in 10 ml of tetrahydrofuran, added with 0.5 ml (3.5 mmole) of triethyl amine and cooled down to the same temperature. While being cooled down in an ice bath and intensively stirred, the solutions of the dipeptide with oxybenzotriazol and carbodiimide are combined, and in 10 minutes the solution of proline benzyl ester tosylate is added. Reactive mixture is stirred with ice for 3 hours and for 24 hours more at room temperature. Fallout dicyclohexylurea is filtered out, the filtrate is removed in vacuum; residue is dissolved in ethyl acetate (100 ml). The solution is washed successively with 0.5 N sulfur acid, water, 5% sodium bicarbonate solution, water, and dried over waterless sodium sulfate. Ethyl acetate is removed in vacuum, the residue is crystallized in ethyl acetate/hexane system. Re-crystallization is performed from isopropanol. After drying in vacuum, 0.83 g of the product (65%) is obtained. $R_f$=0.86 (benzene-acetone 1:1).

4) H-Glu-Asp-Pro-OH (IV),
glutamyl-aspartyl-proline

Protected tripeptide BOC-Glu(OBzl)-Asp(OBzl)-Pro-OBzl (III) (0.8 g) is dissolved in the mixture of methyl spirit-water (3:1) (20 ml) and hydrated over catalyst Pd/C (5%) for 4 hours. Catalyst is filtered out, solvent is removed in vacuum, residue is dried in vacuum over KOH and $P_2O_5$. Then the product is dissolved in 10 ml of chlorous methylene-trifluoracetic acid (5:1) and held at room temperature for 2 hours. The fullness of unblocking reaction is controlled by TLC in acetonitrile-water system (1:3). The solvent is removed in vacuum; residue is dried in vacuum over KOH.

For purification, 290 mg of the substance is dissolved in 4 ml of 0.01% trifluoracetic acid and subjected to highly productive liquid chromatography on a reverse phase column 50×250 mm Diasorb-130-C16T, 7 µm. Chromatograph Beckman System Gold, 126 Solvent Module, 168 Diode Array Detector Module. Conditions of chromatography: A: 0.1% TFA; B: MeCN/0.1% TFA, gradient B 0→50% in 100 min. Sample volume 5 ml, detection at 215 nm, scanning at 190-600 nm, flow rate 10 ml/min. Main peak fraction is selected. Solvent is removed in vacuum at the temperature not higher than 40° C., removal is multiply (not less than 5 times) repeated with 10 ml of 10% acetic acid solution.

Ultimately the residue is dissolved in 20 ml of deionized water and lyophilized. 125 mg of purified substance in the form of white amorphous powder without smell is obtained.

5) Analysis of the Product

Base substance content is identified by HPLC on the column Phenomenex C 18 LUNA 4.6×150 mm. A: 0.1% TFA, B: MeCN; grad.B 0-100% in 10 min. Flow rate 1 ml/min. Detection at 220 nm, scanning at 190-600 nm, sample 20 µl. Base substance content 97.19%.

TLC: individual, $R_f$=0.67 (acetonitrile-water 2:1, Sorbfil plates, silicagel 8-12 µm, development with chlorine/benzidine).

Humidity content: 6% (gravimetrically, judging by weight loss when drying 20 mg at 100° C.).

pH of 0.01% solution: 4.7 (potentiometrically).

Specific rotary power: $[\alpha]_D^{22}$: −29° (c=1, $H_2O$), "Polamat A", Carl Zeiss Jena.

EXAMPLE 2

Effect of Peptide H-Glu-Asp-Pro-OH on the Development of Thymus and Spleen Explants Taken from Old Rats The experiments were staged on 35 fragments of the thymus and 45 fragments of the spleen taken from rats aged 24 months. Nutritional medium for cultivation consisted of 35% Eagle's solution, 25% calf fetal serum, 35% Hanx solution, 5% chicken embryonic extract, with the addition of glucose (0.6%), insulin (0.5 U/ml), penicillin (100 U/ml), glutamin (2 mM). Thymus and spleen fragments were placed into this medium and cultivated in Petri dishes in a thermostat at 36.7° C. for 48 hours.

Peptide H-Glu-Asp-Pro-OH was added into the experimental medium in concentrations of 0.5, 10 and 100 ng/ml.

Area index (AI)—the ratio of total explant area including the growth zone to the initial area of thymus or spleen fragment was used as a criterion for measuring the biological activity. AI values were expressed in percent, control AI value being taken as 100%.

Figure 1:
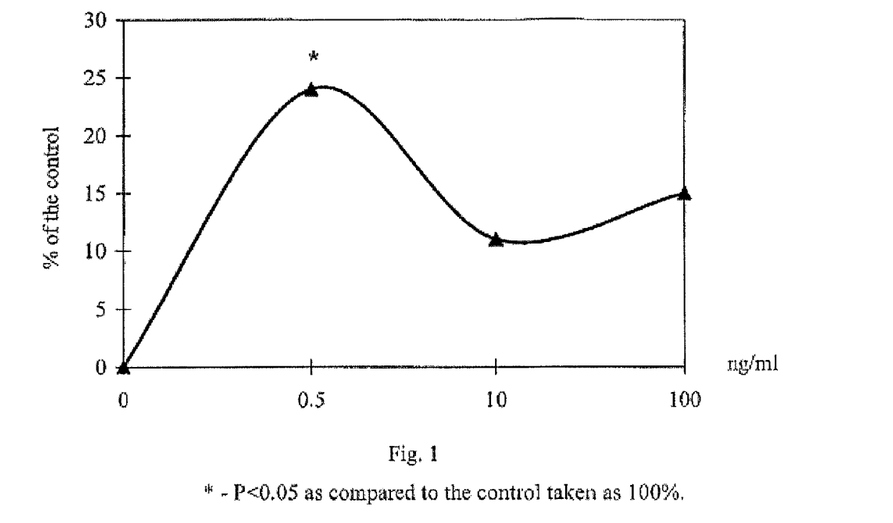
FIG. 1 shows the effect of peptide H-Glu-Asp-Pro-OH on the development of old rats' thymus explants.

It was found, that after 24 hours of cultivation the explants spread over the collagen layer, and proliferating and migrating cells began going out to the periphery of the explant. By the 3$^{rd}$ day of cultivating in case of peptide concentration 0.5 ng/ml AI in thymus explants was reliably increased by 24% as compared to the control AI values (FIG. 1). The study of thymus explants during longer terms of cultivation (7 days) revealed similar stimulation activity of the peptide in the same concentration.

Figure 2:
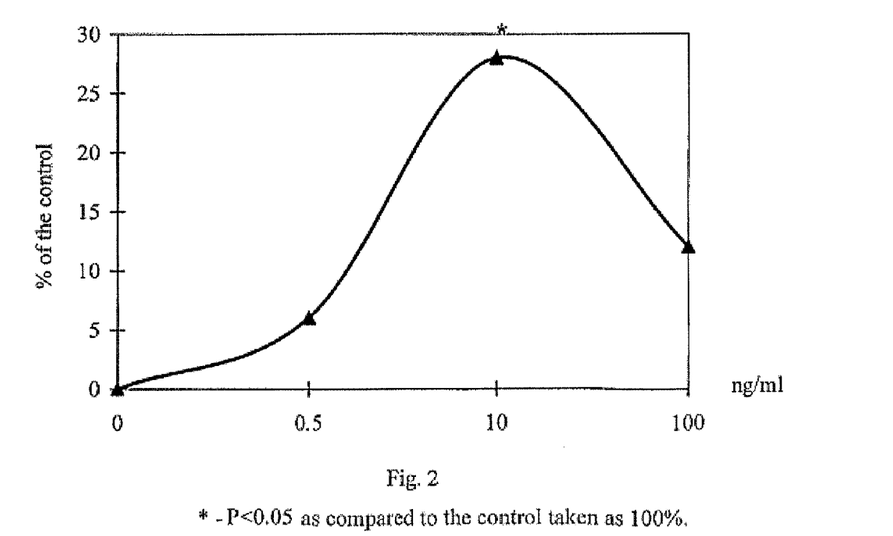
FIG. 2 displays the effect of peptide H-Glu-Asp-Pro-OH on the development of old rats' spleen explants.

The cultivation of spleen explants with peptide H-Glu-Asp-Pro-OH revealed a reliable increase in explants' AI by 28% in case of peptide concentration 10 ng/ml (FIG. 2). By the 7$^{th}$ day of the study the stimulating effect of the peptide in the same concentration was still visible, although it was less pronounced.

Thus, peptide H-Glu-Asp-Pro-OH demonstrated its tissue specific effect on thymus and spleen tissues of old rats, which was manifested in the stimulation of explants' growth.

EXAMPLE 3

Effect of Peptide H-Glu-Asp-Pro-OH on the Production of Lymphocyte Activation Factors in Mice of Different Age Changing production of lymphocyte activation factors (LAF), including cytokines IL-1, IL-6 and FNOA, by mononuclear phagocytes is one of informative indices reflecting the functions of the immune system.

The peculiarities of LAF production by peritoneal macrophages in young and ageing mice, as well as the influence of peptide H-Glu-Asp-Pro-OH on this index were studied. LAF activity of the macrophages was estimated judging by their ability to exert a comitogenic effect on the proliferation of thymocytes, stimulated by suboptimal lectin doses in vitro.

It was found, that resident macrophages in ageing mice in the age of 19-20 months old mice, as well as in the young animals aged 2 months, do not produce LAF without extra stimulation. LAF production by macrophages after their stimulation with LPS is less pronounced in ageing mice, than in young animals.

Study results showed, that peptide H-Glu-Asp-Pro-OH, being introduced into the cultural medium in successive dilutions until the ultimate concentration—from 0.5 to 500 ng/ml, induces the production of LAF by non-stimulated peritoneal macrophages of ageing mice and increases the production of LAF under the effect of LPS. The same tendency to the change in LAF production by macrophages was observed under the effect of peptide H-Glu-Asp-Pro-OH in young mice, but not in the whole range of studied concentrations.

Data showed that age-related change in LAF production by macrophages is one of the mechanisms underlying immune system disorders, and that peptide H-Glu-Asp-Pro-OH may be used for their correction.

EXAMPLE 4

Effect of Peptide H-Glu-Asp-Pro-OH on Proliferative Activity of the Thymus Epithelium Cells in Ageing Cell Cultures The study was staged in vitro in the culture of thymus epithelium cells, which were represented by cells of suspension line VTEC2.H/S, obtained by transforming thymus epithelial cells of human embryo thymus with the material containing SV40 virus, and subsequent cloning of transformed cells.

Peptide H-Glu-Asp-Pro-OH was introduced into cell cultures in successive dilutions to ultimate concentrations of 2, 20 and 200 ng/ml. Proliferation of thymus epithelium cells subjected to 1, 4 and 7 passages was estimated using a radiometrical method, judging by the content of $^3$H-thymidin.

It was found, that peptide H-Glu-Asp-Pro-OH in three tested concentrations significantly enhanced the proliferation of thymus epithelium cells, especially on the $7^{th}$ passage, the most pronounced effect of the peptide being visualized in the concentration of 200 ng/ml (Table 1).

Experimental data point out the capacity of peptide H-Glu-Asp-Pro-OH to enhance the proliferation of thymus epithelium cells in old cultures, which substantiates the immunogeroprotective effect of the peptide.

EXAMPLE 5

Effect of Peptide H-Glu-Asp-Pro-OH on Rat Thymus Cells in Case of Premature Aging, Induced by Ionizing Irradiation The experiments were conducted on 40 male Wistar rats 2 months old, weighing 180-210 g. Premature aging was modeled by gamma irradiation using LUCH-1 machine (source 60Co; dose output $17.166 \times 10^{-4}$ Gy/sec.). The animals were irradiated in the dose of 6 Gy daily for 5 days. All the animals were divided into 6 groups:

1 and 1a—intact rats;
2 and 2a—irradiated rats;
3 and 3a—irradiated rats, subjected to subcutaneous injection of peptide H-Glu-Asp-Pro-OH in the dose of 0.5 μg per animal in 0.25 ml of sterile 0.9% NaCl solution in 24 hours after the first performance of irradiation for 10 days.

Animals of the 2 and 2a group received 0.9% NaCl solution in the same volume and following the same scheme. Slaughtering of the animals and extraction of their thymus were conducted using nembutal anaesthesia (50 mg/kg). Thymus in groups 1-3 was extracted on the 14th day after the experiment onset, in the 1a-3a groups—on the 21 day after the experiment onset.

Fragments of the extracted thymus were fixed for 24 hours in Buen sour liquid for optic microscopy. Material dehydration and filling it in with paraffin for optic microscopy were conducted according to conventional techniques. Paraffin sections (7 μm) were placed on a microscope slide covered with a poly-L-lysine film (Sigma). Histological and immunohistochemical examinations were carried out using Jenamed-2 microscope (Zeiss).

Review staining of the preparations was conducted by hematoxylin-eosin. Mast cells were selectively stained using 1% toluidine blue (Fluka) solution in 0.5M HCl with pH 0.5.

For electron microscopy fragments of the extracted thymus were fixed according to Karnovsky's method. Material dehydration and filling it in with paraffin for optic microscopy, as well as epone mixture for ultra-structural examination were prepared according to generally accepted techniques. Ultra-thin sections (100 nm) prepared on LKB-7A microtome (LKB) were contrasted with uranyl acetate and plumbum citrate. Electron microscopy was conducted in electronic JEM-100S microscope (Jeol).

In order to study cellular proliferative activity there were used mice monoclonal antibodies to proliferative cell nuclear antigen (proliferative cell nuclear antigen—PCNA, clone PC10, Calbiochem, titre 1:50). The immunohistochemical reaction was visualized according to avidin-biotin-peroxidase method (ABP-kit, Vectastain kit) in order to reveal mice immune globulins.

The morphometric studies were conducted by means of the system for computer analysis of microscopic images Imstar using Morphostar and Colquant-2 software, in accordance with the basic principles of stereology and morphometry. For each animal the estimation of the correspondent structures was conducted in 10 visual fields. The test area constituted not less than 10 000 thymocytes nuclei. The number of mast cells in the thymus was estimated in the area of not less than 5 mm$^2$. Proliferative activity index ($I_{PCNA}$) was calculated using the following formula: $I_{PCNA}(\%) = N_{PCNA}/N_{nuclei} \times 100$.

Optic microscopy of the histological sections, stained with hematoxylin-eosin, showed that control animals' thymus has lobate structure. Lobules shape and size are variable. Between the lobules there are identified thin connective tissue strata, including small blood vessels. Inside the lobules there are distinctly identified the cortex being from the outside, and the medulla located in the centre.

Inside the cortical layer there are mainly non-fissionable small thymic lymphocytes, located between epithelial cells of the cortex. Epithelial cells are not numeral, star-shaped due to long and thin cytoplasmic sprouts, which together constitute a network, where the cortical thymocytes are located. Thymocytes have roundish well stained nucleus with nucleoli. In the medulla there are mostly epithelium cells, the lymphocytes are essentially fewer in number than in the cortex.

On the $14^{th}$ and the $20^{st}$ days after the irradiation (2, 2a groups) on the histological sections stained with hematoxylin-eosin, there is registered a disorder in the structural organization of the thymus, which is seen first of all in atrophic changes. The number of lobules and their size are significantly reduced. The division into cortex and medulla effaces, the verge between the layers almost disappear. In the medulla the number of lymphocytes is slightly increased. The correlation between the parenchyma and stroma is upset, the last been prevailing. Cortical thymocytes are mostly represented by big or medium lymphocytes. In the Hassall's corpuscles there are registered cellular decay and degeneration.

Microscopic analysis of the thymic preparations of the animals, which had been subjected to peptide H-Glu-Asp-Pro-OH injection after the first irradiation performance (3, 3a groups), revealed less pronounced involution changes as compared to those in the animals in the 2 and 2a groups.

Electronic microscope study of the thymus of the control groups animals revealed that in the cortex of the lobules the thymocytes form gatherings consisting of cells with similar size and morphologic structure. These cells have big nuclei with condensed chromatin at the periphery, one or two big nucleoli, and narrow cytoplasmic rim, containing small number of mitochondria and polyribosomes. Among these cells there are large thymocytes, having wider cytoplasmic rim and containing a larger number of mitochondria, they are so called activated lymphocytes.

Mast cells are registered in the interlobular connective tissue, close to blood vessels. Epithelial reticular cells, which are more easily identified in the lobular cortex, are finely-branched, have a crumbly nucleus of irregular shape and cytoplasm rich in endoplasmic reticulum tubules.

In case of irradiation ageing, the animals of the 2 group showed among the most pronounced changes in the thymus such changes as exfoliation of parts of the outer nuclear membrane, disordered tight contact between single thymocytes. Nevertheless irradiation does not reduce the number of thymocytes being on different phases of mitosis.

Among the mast cells there were registered differences in reaction to irradiation. Some cells did not differ in structure from mastocytes of control animals, while others revealed the formation of spacious vacuoles, inside which there could be up to 10 secretory granules of different electron thickness showing different stages of secretory material lysis. In epithelial reticular cells there were revealed significant exfoliation of the outer membrane, widening of the endoplasmatic reticulum membranes, emerging of numerous small vacuoles, swelling and lysis of mitochondria crystas.

On the $21^{st}$ day after the experiment onset in the animals, exposed to irradiation ageing (2a group) there were not registered any pronounced changes in the cortex of thymic lobules as compared to the 2 group.

In animals subjected to peptide H-Glu-Asp-Pro-OH injection, in case of irradiation ageing model on the 14 day after the irradiation course onset there weren't registered any pronounced changes in thymocytes. They tightly adjoin to each other in the cortex of the thymus, have nuclei of relatively the same size with one or two nucleoli. Cytoplasmic rim is very thin, there are registered single mitochondria, in which are easily identified crystas. In epithelial reticular cells there is registered a mild exfoliation of karyolemma and reduction in cytoplasm vacuolization.

On the $21^{st}$ day after the irradiation the animals subjected to peptide H-Glu-Asp-Pro-OH injection (group 3a) revealed gathering of the mast cells not only in interlobal connective tissue, but also in the cortex of the thymus lobules. Electronic microscope study of the thymus in the animals exposed to irradiation and treated with peptide H-Glu-Asp-Pro-OH, revealed granular leukocytes, as well as plasmatic cells, forming small groups. There are no pronounced morphologic changes in the epithelial reticular cells, but the number of secretory granules in their cytoplasm reduces.

Thus, the conducted studies showed that after the fractionated irradiation in the diapason of sub-lethal doses, modeling premature aging, in the thymus of the animals, subjected to peptide H-Glu-Asp-Pro-OH injection, there are defined peculiarities of structural-functional organization, which are seen mostly on ultrastructural level. Infiltration of the cortex with granular leucocytes and plasmatic cells in this case is probably connected to the intensification of reparative processes, as it is known that granulocytes are sensitive to activation by different humoral and cellular factors. Gathering of the mast cells in the cortex might be explained by the fact that for the final differentiation of mastocytes the IL-3, produced by T-lymphocytes, is necessary.

Computer analysis of microscopic images of the 1 group revealed that the main population of proliferating cells in the thymus of intact animals ($I_{PCNA}$=26%) is located in the cortex and tends to concentrate in peripheral areas of the lobules, which are contoured by connective tissue partition. In the thymus of the control group animals the mast cells constitute a relatively small fraction of cells (16±2 per 1 mm$^2$) and are amassed in the form of special chains in thin connective tissue partitions. In the 2 group PCNA-positive nuclei are mainly amassed in peripheral area of the reduced lobules. It is significant that there takes place an increase in the number of the mast cells in the connective tissue partitions (27±3). High $I_{PCNA}$ and hyperplasia of the mast cells evidence the onset of the post-irradiation thymus restoration. In the group 3 under the effect of peptide H-Glu-Asp-Pro-OH in the thymus there is registered an activation of reparative processes according to the indices of proliferation. $I_{PCNA}$ reaches 55%. There is registered a proliferative activity in extramedullar areas of hematosis. There is registered a pronounced increase in the number of mast cells in the thymus of irradiated animals after peptide H-Glu-Asp-Pro-OH injection (32±5).

Computer analysis of microscopic images showed that irradiated animals subjected to peptide H-Glu-Asp-Pro-OH injection report an increase in the proliferative potential of cells. These data show that peptide H-Glu-Asp-Pro-OH exerts positive effect on arresting remote consequences of irradiation and thus exert immune geroprotective effect in case of irradiation model of premature aging.

EXAMPLE 6

Effect of Peptide H-Glu-Asp-Pro-OH on Chromatin in Blood Lymphocytes in Old Patients in vitro It is known that active chromatin is an obligatory condition for genes transcriptional activity. In case of aging there takes place an intensive process of heterochromatinization associated with inactivation of genes which were active before.

Peptide H-Glu-Asp-Pro-OH effect on the system of chromatin domains was studied in old people lymphocytes cultures, in particular on chromatin reactivation such as in dehet-erochromatinization of heterocliromatin satellite filaments (activity of synthetic processes in ribosomal genes, total heterochromatin, structural heterochromatin (changeability of C-blocks of the 1, 9 and 16 chromosomes) and optional heterochromatin.

The studies were conducted on the chromosomes of 150 PHA-stimulated and 40 PHA-non-stimulated lymphocyte cultures, obtained from 95 healthy patients aged 75-88 (control—25 donors aged 20-40). There were studied 2 cell cultures from each patient —one intact and one with peptide H-Glu-Asp-Pro-OH added into the cultural medium up to the ultimate concentration of 0.01 µg/ml. To study each parameter there were analyzed from 30 up to 50 metaphases of both intact lymphocyte cultures and those with added peptide (10 cultures of each).

To estimate ribosomal genes activity in intact cultures and under the effect of the peptide there were used methods of Ag-banding and of the registration of nucleolar organizers regions (NOR) of acrocentric chromosomes. Changeability of the activity level was estimated comparing two binomial totals.

Polymorphism of structural C-heterochromatin of the 1, 9 and 16 chromosomes was estimated. For comparative analysis of C-stained chromosomes of intact cultures and those treated with the peptide there was used a standard system of classification, according to which the size of the 1, 9, 16 chromosomes C-segments were compared to the chromosome 16 short leg and the results were divided into 5 categories—a, b, c, d, e. The changeability of facultative heterochromatin was estimated according to the frequency of sister chromatid exchange (SCE) in intact and peptide-treated lymphocytes.

The analysis of the frequency of Ag-positive NOR identification shows that the extent of argentophilic character of definite acrocentrics differs in the control and in peptide-treated cellular cultures (Table 2). It was revealed that the number of Ag-positive NOR associating acrocentrics per one cell in cultures finished with the peptide is statistically reliably decreased as compared to the indices of control group cultures from old patients. It should be emphasized, that the effect of peptide H-Glu-Asp-Pro-OH entailed a uniform growth of the frequency of DD-, DG- and GG-types associations.

Increase in the number of Ag-positive NOR and frequency of acrocentric chromosomes associations in lymphocyte cultures under the effect of peptide H-Glu-Asp-Pro-OH points out the heterochromatinization of satellite filaments, providing for the activation of ribosomal genes in case of aging.

It was found, that peptide H-Glu-Asp-Pro-OH expands the upper levels of chromatin organization and promotes deheterochromatinization of the total (optional and structural) heterochromatin in the lymphocytes of old patients (Table 2).

The indices of heteromorphism (reduction of large blocks) of the structural heterochromatin (C-segments) are displayed in Table 2 separately for 1, 9 and 16 chromosomes in the cultures of intact lymphocytes from old patients, as well as of those treated with peptide H-Glu-Asp-Pro-OH. In case of peptide H-Glu-Asp-Pro-OH administration chromosomes 1 and 9 were found to be heteromorphic. In this case the level of heteromorphism for the mentioned chromosomes is statistically reliable.

It is known that chromosomes 1 and 9 have a pronounced variability of absolute and relative C-heterochromatin size in case of some pathologies and under the effect of some chemical agents, while the distribution of heterochromatin C-segments in chromosomes 16 remains stable. Besides, there is registered a reliable increase in C-segments of chromosome 1 (heterochromatinization of precentromere heterochromatin) in old patients.

Data show that peptide H-Glu-Asp-Pro-OH effect on lymphocytes provides for the reduction chromosomes 1 and 9 C-blocks size, which points out the ability of the peptide to selectively induce decondensation (deheterochromatinization) of structural heterochromatin in cells of old patients.

Peptide H-Glu-Asp-Pro-OH induced increase of sister chromatid exchange frequency in cells of old patients (Table 2). The revealed increase in SCE indices in lymphocytes taken from old patients takes place due to heterochromatinizated euchromatin chromosome regions decondensation, entailed by peptide H-Glu-Asp-Pro-OH effect.

Thus, peptide H-Glu-Asp-Pro-OH induces the decondensation of densely packed chromatin fibrils, this correlates to the restoration of the expression of the genes, repressed as a consequence of euchromatin chromosome regions heterochromatinization in case of aging.

EXAMPLE 7

Study of Peptide H-Glu-Asp-Pro-OH Toxicity

Common toxicity of H-Glu-Asp-Pro-OH was studied according to the requirements stated in the "Manual for experimental (pre-clinical) study of new pharmacological substances" (2005): acute toxicity in case of single administration of the substance and sub-acute and chronic toxicity in case of long-term administration of the peptide.

The study of acute toxicity was performed on 60 white mongrel male mice with body weight of 18-21 g. The animals were randomly subdivided into 6 equal groups. The substance was administered to the animals once, intramuscularly, in the doses of 1 mg/kg, 2 mg/kg, 3 mg/kg, 4 mg/kg, 5 mg/kg in 0.25 ml of sterile 0.9% NaCl solution. The control animals received 0.9% NaCl solution in the same volume. The study of subacute toxicity was performed on 50 white mongrel male rats with body weight of 170-210 g. Experimental animals received the substance daily, intramuscularly for 90 days in the doses of 1 μg/kg, 0.1 mg/kg, 1 mg/kg in 0.5 ml of sterile 0.9% NaCl solution. Control animals received sterile 0.9% NaCl solution in the same volume. Morphology and properties of the animals' peripheral blood were studied before the administration of the substance, as well as on the $30^{th}$, $60^{th}$ and $90^{th}$ day after the beginning of the administration. Upon completion of the experiment biochemical and coagulologic indices of the blood were also evaluated. The studies of chronic toxicity were conducted for 6 months, basing on the term of recommended clinical administration of the substance, on 80 male guinea pigs with body weight of 280-310 g. Experimental animals received the peptide daily, once a day, intramuscularly, for 6 months in the doses of 1 μg/kg, 0.1 mg/kg, 1 mg/kg in 0.5 ml of sterile 0.9% NaCl solution. Control animals received sterile 0.9% NaCl solution in the same volume and by the same schedule. Traditional methods were used for the evaluation of the following indices of the animals' peripheric blood: the quantity of erythrocytes, hemoglobin, reticulocytes, thrombocytes, leukocytes, leukocyte formula, erythrocyte sedimentation rate (ESR), erythrocyte resistance. Alongside with that, the content of total protein in the serum was identified using Lowry's method, as well as potassium and sodium content using the method of plasma spectrophotometry. After the completion of the experiment pathomorphologic studies of animal brain and spinal cord, spinal cord ganglia, thyroid gland, parathyroid glands, adrenal glands, testis, pituitary body, heart, lungs, aorta, liver, kidneys, urinary bladder, pancreas, stomach, small intestine, large intestine, thymus, spleen, lymph nodes and bone marrow were performed. The study of acute toxicity showed, that a single administration of the studied peptide to animals in the dose exceeding the therapeutic one, which is recommended for clinical administration, by more than 5000 times, does not cause toxic reactions, which points out the width of diapason of possible therapeutic doses of the substance. The study of subacute and chronic toxicity of the peptide showed the absence of any side effects in case of long-term administration of the substance in doses exceeding the therapeutic one by 100-1000 times. The study of peptide effect on blood morphology and biochemical indices, as well as on erythrocyte sedimentation rate (ESR), erythrocyte resistance showed that no statistically significant changes in the studied indices took place (Table 3).

The evaluation of the animals' general status, of morphologic and biochemical indices of peripheral blood, of morphological status of the organs, of the status of cardiovascular and respiratory systems, as well as of liver and kidney functions revealed no pathologic alterations in the organism.

The absence of common toxicity allows to recommend the pharmaceutical composition, containing peptide H-Glu-Asp-Pro-OH as its active base, for clinical studies.

EXAMPLE 8

Efficiency of Peptide H-Glu-Asp-Pro-OH Application in Elderly Patients with Age-related Immune Status Decline It is known that different factors of chemical, physical and biological nature, depending on the duration and intensity of their effect on the human organism, might lead to the emaciation of the adaptive and compensatory mechanisms and induce serious disorders in different segments of the immune system. Pathologic disorders in the immune system as a rule contribute to longer duration of the main disease and a tendency to relapses, to a decrease in organism resistibility to infections and to the development of severe complications. Elderly and old people constitute special groups of patients, characterized by an age-related decrease in the immune status and usually suffering from several diseases, which are aggravated by immune system disorders.

The efficacy of pharmaceutical composition, containing an effective amount of peptide H-Glu-Asp-Pro-OH as an active base, was studied in elderly and old patients, exposed to long-term ionizing irradiation in small doses.

The main group consisted of 38 elderly patients (18 men, 20 women), who were divided into 3 groups according to the intensity of immune status changes. In case of significantly altered immune status, associated with considerable worsening of the general status, the patients together with conventional means of treatment also received the pharmaceutical composition, containing peptide H-Glu-Asp-Pro-OH, in the dose of 5.0 mg in 1.0 ml of sterile 0.9% NaCl solution intramuscularly, daily, once a day for 10 days, in case of medium severity of immune status disorders—in the dose of 10.0 µg in 1 ml of sterile 0.9% NaCl solution intramuscularly, daily, once a day for 10 days. Elderly and old patients with age-related decrease of the immune functions were injected with the pharmaceutical composition containing peptide H-Glu-Asp-Pro-OH in the dose of 10.0 µg in 1 ml of sterile 0.9% NaCl solution intramuscularly, daily, once a day for 10 days. 32 control group patients (14 men, 18 women) received only conventional treatment. The patients of both groups were from 62 to 83 years old. The efficacy of the pharmaceutical composition containing peptide H-Glu-Asp-Pro-OH was estimated judging by the dynamics of the patients' complaints and a set of objective indices, such as common blood and urine tests, immunologic study of peripheral blood (the number of T- and B-lymphocytes was estimated using the immunofluorescence method with monoclonal antibodies to CD3, CD4, CD8, CD20 differentiation lymphocytes antigens; content of immunoglobulins of different classes—using Mancini's method of radial immunodiffusion in the gel, T-lymphocytes functional activity—in lymphocyte migration inhibition reaction (LMIR) with Con A.

The conducted studies showed that 92% of patients living in environmentally unfavorable regions had immune status disorders manifested in the reduced number of CD3+, CD4+ cells together with a slight increase in the number of lymphocytes with CD8+ phenotype, which evidences the reduced organism immunoreactivity (disordered CD4+/CD8+ ratio). The results of LMIR with Con A show a decrease in the functional activity of T-lymphocytes (mainly CD8+, i.e. T-suppressors/killers). The number of CD20+-cells, constituting B-lymphocytes population, did not reliably differ from normal indices, but at the same time there was registered an increase in the quantity of M and G immunoglobulins in the blood serum of elderly patients, which points out disorders in this component of immune system as well (Table 4). It should be noted that the quantitative indices of CD3+ and CD4+ cells content are characteristic for the lower limit of physiological fluctuation of their quantity in old patients, which evidences the exhaustion and premature aging of the immune system. As a rule, people with secondary immunodeficiency reveal a pronounced asthenic syndrome and significant changes in cardiovascular system. The results of the conducted studies clearly show that the pharmaceutical composition containing peptide H-Glu-Asp-Pro-OH in different doses is an effective means of correction of secondary immunodeficiencies, which develop in response to the extreme factors and characterize premature aging of the organism. Application of the pharmaceutical composition containing peptide H-Glu-Asp-Pro-OH in different doses depending on the degree of the immune status disorder, in complex with the symptomatic means allowed to normalize disordered immune system indices in 82% of the patients (in 56% of the patients of the control group).

The data displayed in Table 4 shows that the most pronounced effect of peptide H-Glu-Asp-Pro-OH was registered in T-lymphocytes populations with respect to their functional activity (reliable increase in CD3+ and CD4+-lymphocytes content, normalization of CD4+/CD8+ ratio). Less evident reaction was registered in B-system of the immunity, probably due to its being more conservative. Nevertheless there is a definite tendency to the normalization of immunoglobulins M and G content, at the same time the patients who received peptide H-Glu-Asp-Pro-OH, showed a decrease in these indices to the age-specific norm (1.65 and 15.45 g/l correspondingly). After the treatment course using the pharmaceutical composition containing peptide H-Glu-Asp-Pro-OH in different doses, elderly people in the three main groups, exposed to small doses of ionizing irradiation, reported significant improvement of the general state and reduction of the asthenic syndrome, which is always associated with secondary immunodeficiencies.

Thus, the application of the pharmaceutical composition containing peptide H-Glu-Asp-Pro-OH as its active base in different doses depending on the severity of the immune status disorders, improves the status of elderly and old patients, exposed to long-term ionizing irradiation in small doses, normalization of cellular and humoral immunity indices, does not exert any side effects, complications or drug addiction and can be used as a means for prevention and treatment together with any other means of symptomatic and pathogenic therapy, which are used for correcting secondary immunodeficiencies (immunomodulators, adaptogens, vitamins etc.).

TABLE 1

| Variant of experiment | Dose, ng/ml | $1^{st}$ passage | $4^{th}$ passage | $7^{th}$ passage |
|---|---|---|---|---|
| Control | 0 | 1560 ± 93 | 715 ± 54 | 523 ± 32 |
| Peptide H-Glu-Asp-Pro-OH | 2 | 1480 ± 89 | 730 ± 54 | 705 ± 46* |
|  | 20 | 1585 ± 95 | 680 ± 48 | 680 ± 41* |
|  | 200 | 1530 ± 91 | 760 ± 58 | 795 ± 49* |

*P < 0.05 as compared to the control.

TABLE 2

| Variant of experiment | Associated acrocentric chromosomes (per cell) | Deheterochromatinization of optional heterochromatin - SCE (per cell) | Total heterochromatin | Structural heterochromatin (C-blocks) Chromosomes | | |
|---|---|---|---|---|---|---|
| | | | | 1 | 9 | 16 |
| Control (20-40 years) | 1.33 ± 0.06 | 7.7 ± 0.4 | Stable status | Stable status | Stable status | Stable status |
| Control (75-88 years) | 1.17 ± 0.05* | 5.9 ± 0.2* | Heterochromatinization | Heterochromatinization | Stable status | Stable status |
| Peptide H-Glu-Asp-Pro-OH | 2.32 ± 0.12** | 8.4 ± 0.5** | Deheterochromatinization | Deheterochromatinization | Deheterochromatinization | Stable status |

*$P < 0.05$ as compared to the control (20-40 years);
**$P < 0.001$ as compared to the control (75-88 years).

TABLE 3

| | Administration of peptide H-Glu-Asp-Pro-OH (1 μg/kg) | | | |
|---|---|---|---|---|
| | 3 months | | 6 months | |
| Index | Control (n = 24) | Peptide (n = 24) | Control (n = 24) | Peptide (n = 24) |
| Erythrocytes, ×$10^{12}$/l | 5.3 ± 0.6 | 5.4 ± 0.1 | 5.4 ± 0.3 | 5.3 ± 0.5 |
| Hemoglobin, g/l | 14.2 ± 1.4 | 13.9 ± 1.0 | 14.5 ± 1.3 | 14.4 ± 0.7 |
| Reticulocytes, % | 1.3 ± 0.07 | 1.3 ± 0.06 | 1.1 ± 0.05 | 1.2 ± 0.09 |
| Thrombocytes, ×$10^9$/l | 143.7 ± 7.9 | 142.4 ± 3.8 | 144.5 ± 8.6 | 143.1 ± 6.1 |
| Leukocytes, ×$10^9$/l | 9.4 ± 0.5 | 10.1 ± 0.4 | 9.6 ± 0.5 | 9.9 ± 0.3 |
| Stab neutrophils, % | 0.31 ± 0.04 | 0.28 ± 0.06 | 0.33 ± 0.04 | 0.32 ± 0.03 |
| Segmented neutrophils, % | 45.8 ± 2.1 | 45.4 ± 1.9 | 46.2 ± 3.5 | 44.2 ± 2.7 |
| Eosinophils, % | 0.69 ± 0.05 | 0.67 ± 0.07 | 0.72 ± 0.04 | 0.68 ± 0.06 |
| Basophils, % | 0.61 ± 0.04 | 0.66 ± 0.09 | 0.72 ± 0.03 | 0.65 ± 0.07 |
| Monocytes, % | 2.5 ± 0.02 | 2.6 ± 0.01 | 2.6 ± 0.06 | 2.4 ± 0.04 |
| Lymphocytes, % | 48.9 ± 2.5 | 49.6 ± 2.1 | 51.3 ± 2.7 | 50.6 ± 2.5 |
| ESR, mm/hour | 1.69 ± 0.05 | 1.76 ± 0.04 | 2.01 ± 0.05 | 1.87 ± 0.02 |
| Erythrocyte resistance, % NaCl | | | | |
| maximum | 0.41 ± 0.02 | 0.42 ± 0.01 | 0.42 ± 0.04 | 0.43 ± 0.06 |
| minimum | 0.32 ± 0.05 | 0.31 ± 0.05 | 0.34 ± 0.04 | 0.33 ± 0.04 |
| Total protein in the blood serum, g/l | 72.9 ± 3.1 | 73.8 ± 2.5 | 73.1 ± 3.4 | 72.7 ± 2.9 |
| Sodium in the blood serum, mmole/l | 153.9 ± 5.7 | 152.4 ± 3.9 | 155.5 ± 6.2 | 153.5 ± 4.5 |
| Potassium in the blood serum, mmole/l | 5.1 ± 2.3 | 5.2 ± 2.5 | 5.2 ± 2.1 | 5.1 ± 1.9 |

TABLE 4

| Index | Before treatment | After conventional treatment | After treatment including the administration of peptide H-Glu-Asp-Pro-OH |
|---|---|---|---|
| Leukocytes, ×$10^9$/l | 5.0 ± 0.2 | 5.4 ± 0.1 | 5.6 ± 0.1 |
| Lymphocytes, % ×$10^9$/l | 26.2 ± 2.6 | 31.4 ± 2.4 | 35.1 ± 2.1 |
| | 1.51 ± 0.08 | 1.64 ± 0.05 | 1.87 ± 0.05 |
| CD3+, % ×$10^9$/l | 43.5 ± 2.3 | 49.3 ± 2.2* | 55.7 ± 2.6*# |
| | 1.43 ± 0.09 | 1.60 ± 0.07* | 1.86 ± 0.05*# |
| CD4+, % ×$10^9$/l | 28.5 ± 2.8 | 30.8 ± 2.1 | 34.6 ± 2.0* |
| | 0.41 ± 0.01 | 0.49 ± 0.07 | 0.67 ± 0.09* |
| CD8+, % ×$10^9$/l | 26.4 ± 1.5 | 25.7 ± 1.6 | 24.9 ± 1.8 |
| | 0.43 ± 0.05 | 0.42 ± 0.03 | 0.46 ± 0.07 |
| CD4+/CD8+ | 1.1 | 1.2 | 1.4*# |
| CD20+, % ×$10^9$/l | 12.3 ± 0.6 | 12.0 ± 0.4 | 12.0 ± 0.7 |
| | 0.18 ± 0.01 | 0.21 ± 0.01 | 0.20 ± 0.01 |
| LMIR, % | 88.1 ± 5.4 | 76.2 ± 4.8* | 70.4 ± 4.9* |
| IgM, (g/l) | 1.82 ± 0.06 | 1.72 ± 0.05 | 1.64 ± 0.06 |
| IgG, (g/l) | 15.9 ± 1.3 | 15.6 ± 1.6 | 14.9 ± 1.7 |
| IgA, (g/l) | 2.2 ± 0.1 | 2.0 ± 0.1 | 2.1 ± 0.3 |

*$P < 0.05$ - reliable as compared to the index before treatment;
$P < 0.05$ - reliable as compared to the index before conventional treatment.

The invention claimed is:

1. A peptide of the formula H-Glu-Asp-Pro-OH.

2. A pharmaceutical composition comprising the peptide of claim 1 and a pharmaceutically acceptable carrier.

3. The pharmaceutical composition according to claim 2, which is a parenteral formulation.

4. A method of preventing and/or correcting age-related disorders of cellular and humoral immunity in a patient by stimulating the processes of lymphocytes proliferation and differentiation, wherein the method consists of administering to the patient a pharmaceutical composition containing an effective amount of a peptide of the formula H-Glu-Asp-Pro-OH in the dose of 0.01-100 µg/kg of body weight as its active base at least once a day.

5. The method according to claim 4 wherein the composition is administered parenterally.

* * * * *

SEQUENCE LISTING

<160> NUMBER OF SEQ ID NOS: 1

<210> SEQ ID NO 1
<211> LENGTH: 3
<212> TYPE: PRT
<213> ORGANISM: Artificial
<220> FEATURE:
<223> OTHER INFORMATION: Peptide substance H-Glu-Asp-Pro-OH, stimulating
      the processes of lymphocytes proliferation and differentiation by
      restoring the synthesis of tissue specific proteins and by
      normalizing the metabolic and molecular-genetic indices

<400> SEQUENCE: 1

Glu Asp Pro
1